United States Patent
Liu et al.

(10) Patent No.: US 11,307,123 B2
(45) Date of Patent: Apr. 19, 2022

(54) METHOD FOR ANALYZING STABLE ISOTOPES OF PARTICULATE ORGANIC CARBON (POC) AND NITROGEN IN SEAWATER USING ELEMENTAL ANALYSIS-ISOTOPE RATIO MASS SPECTROMETRY (EA-IRMS)

(71) Applicant: YELLOW SEA FISHERIES RESEARCH INSTITUTE, CHINESE ACADEMY OF FISHERY SCIENCES, Qingdao (CN)

(72) Inventors: Yi Liu, Qingdao (CN); Jihong Zhang, Qingdao (CN); Wenguang Wu, Qingdao (CN); Ke Sun, Qingdao (CN)

(73) Assignee: YELLOWSEA FISHERIES RESEARCH INSTITUTE, ACADEMY OF FISHERY SCIENCES, Qingdao (CN)

(*) Notice: Subject to any disclaimer, the term of this patent is extended or adjusted under 35 U.S.C. 154(b) by 0 days.

(21) Appl. No.: 17/451,325

(22) Filed: Oct. 19, 2021

(65) Prior Publication Data
US 2022/0034772 A1     Feb. 3, 2022

Related U.S. Application Data

(63) Continuation of application No. PCT/CN2020/091865, filed on May 22, 2020.

(30) Foreign Application Priority Data

Nov. 18, 2019   (CN) .......................... 201911128334.6

(51) Int. Cl.
*G01N 1/44* (2006.01)
*G01N 27/62* (2021.01)
*G01N 1/42* (2006.01)

(52) U.S. Cl.
CPC ................. *G01N 1/44* (2013.01); *G01N 1/42* (2013.01); *G01N 27/62* (2013.01)

(58) Field of Classification Search
CPC ............. G01N 1/44; G01N 1/42; G01N 27/62
(Continued)

(56) References Cited

U.S. PATENT DOCUMENTS

| 7,514,419 | B2* | 4/2009 | Erion | ........................ | A61P 1/16 514/140 |
| 2017/0082635 | A1* | 3/2017 | Rychnovsky | .......... | G16C 20/50 |
| 2017/0269094 | A1* | 9/2017 | Nitz | ........................ | G01N 33/58 |

FOREIGN PATENT DOCUMENTS

| CN | 1482463 A | 3/2004 |
| CN | 104236989 B | 2/2017 |

(Continued)

OTHER PUBLICATIONS

Shang Chen, et al., Specifications for oceanographic survey-Part 9: Guidelines for marine ecological survey, Chinese National Standard GB/T12763.9-2007, 2007, 23 pages.

(Continued)

*Primary Examiner* — Nicole M Ippolito
(74) *Attorney, Agent, or Firm* — Bayramoglu Law Offices LLC

(57) ABSTRACT

A method for analyzing stable isotopes of particulate organic carbon (POC) and nitrogen in seawater using elemental analysis-isotope ratio mass spectrometry (EA-IRMS), including: using a glass fiber filter membrane to filter a collected water sample and then filter 100 ml of distilled water; subjecting a resulting membrane sample to acidification; and subjecting an acidified membrane sample to EA-IRMS analysis on a machine, where an oxygen addition time is set to 80 s and a combustion tube temperature is set to 700° C. for an elemental analyzer, and a trap current is set to 300 μA to 400 μA for an isotope ratio mass spectrometer.

(Continued)

The method of the present disclosure can reduce a detection cost and improve the data accuracy and work efficiency.

1 Claim, 1 Drawing Sheet

(58) Field of Classification Search
USPC .............................. 250/281, 282, 283, 288
See application file for complete search history.

(56) References Cited

FOREIGN PATENT DOCUMENTS

| CN | 106404488 A | 2/2017 |
|---|---|---|
| CN | 106770606 A | 5/2017 |
| CN | 110672709 A | 1/2020 |
| CN | 110672780 A | 1/2020 |
| JP | 2011164020 A | 8/2011 |
| WO | 2014036077 A1 | 3/2014 |

OTHER PUBLICATIONS

Liu Yi, et al., Spatial-temporal distribution of particulate organic carbon and particulate nitrogen in the mariculture areas of Zhangzhi Island, Marine Sciences, 2016, pp. 9-18, vol. 40, No. 5.

Zhao Guiying, et al., Use of PE-240 II Elemental Analyzers in Chemical Manufacturing, 2002, pp. 97-98, 28.

Sun, Hong, et al., The Determination of Organic Carbon in Total Suspended Particulate Matter, Journal of Qiqihar Light Industry Institute, 1995, pp. 92-94, vol. 11 No. 3.

* cited by examiner

METHOD FOR ANALYZING STABLE ISOTOPES OF PARTICULATE ORGANIC CARBON (POC) AND NITROGEN IN SEAWATER USING ELEMENTAL ANALYSIS-ISOTOPE RATIO MASS SPECTROMETRY (EA-IRMS)

CROSS REFERENCE TO THE RELATED APPLICATIONS

This application is a continuation application of the International Application No. PCT/CN2020/091865, filed on May 22, 2020, which is based upon and claims priority to Chinese Patent Application No. 201911128334.6, filed on Nov. 18, 2019, the entire contents of which are incorporated herein by reference.

TECHNICAL FIELD

The present disclosure belongs to the field of water quality detection, and specifically relates to a method for analyzing stable isotopes of particulate organic carbon (POC) and nitrogen in seawater using elemental analysis-isotope ratio mass spectrometry (EA-IRMS). With the high-efficiency, rapidness, and accuracy of an elemental analyzer and an isotope ratio mass spectrometer, the method of the present disclosure can save consumables, improve data accuracy, and prolong a service life of an instrument.

BACKGROUND

Advanced scientific research facilities and instruments are the keys to technical innovation and breakthrough, which promotes and supports the development of scientific research. At present, China is vigorously developing the "Blue Economy", and emerging fields such as carbon sink fisheries and marine ranches are gradually emerging. "Green", "healthy", and "high efficiency" have become key words for the development of aquaculture, and the traditional extensive aquaculture model has been gradually replaced by the intensive and industrial aquaculture model. However, in the past period of time, driven by economic interests, the aquaculture in China has experienced blind expansion at the expense of the environment. The development of marine aquaculture must follow the principles of green, health and efficient. The construction of modern aquaculture facilities such as artificial reefs and marine ranches is just a new method or measure for the development of green ecological aquaculture. The construction of all ecological aquaculture models requires related research on food webs. With the advent of mass spectrometer, isotopic tracer technique has been successfully applied to the analysis of a food web structure in an ecosystem. Stable isotopes of POC and nitrogen in seawater are key parameters to reveal a material circulation path, a trophic level, a food source, and the like of an ecosystem. However, the lack of standardized and accurate measurement methods results in low data quality and high cost of measurement, which further affects the reliability of scientific research results.

At present, there is no national standard for test methods of stable isotopes of POC and particulate nitrogen (PN) in seawater. However, because an isotope ratio mass spectrometer is generally used in combination with an elemental analyzer, the elemental analysis method of POC and PN can be used for reference. This method is stipulated in the 9th part of GB/T12763.9-2007 Specifications for Oceanographic Survey, where seawater is filtered through a φ25 mm glass fiber filter membrane (burned at 450° C. for 5 h in advance), and then the glass fiber filter membrane is acidified and subjected to determination by an elemental analyzer.

However, this method has a major defect, that is, in each sample analysis process, there is a probability of more than 90% that an internal combustion tube of the elemental analyzer will crack or burst. According to the analysis of long-term accumulated experimental experience, it is mainly caused by the glass fiber material of the filter membrane. After the filter membrane in the combustion tube is burned by the elemental analyzer at a high temperature, the burned glass fiber material may produce some debris, and when the combustion tube is subjected to regular helium purging by the instrument, the debris contacts a tube wall of the quartz combustion tube and adheres to the tube wall at a high temperature. When a temperature decreases at the end of the operation of the instrument, due to thermal expansion and contraction, the tube wall of the internal combustion tube of the elemental analyzer is unevenly stressed and thus cracks. Further, when the instrument is heated once again, due to being unevenly heated, the internal combustion tube bursts at a high temperature and a high pressure inside the instrument. This phenomenon increases a use cost of the instrument, affects a service life of the instrument, reduces a detection accuracy of a sample, and brings more hazards and workload to operators. Because a manufacturer of the instrument believes that a low temperature will cause incomplete combustion of a sample, an instruction manual of the instrument clearly states that an operating temperature must be 950° C. Moreover, the burst of the combustion tube usually occurs during a temperature-rise process of the instrument or a detection process of a sample, and after the burst, debris must be cleaned up in time, otherwise, a service life of the instrument will be compromised. Therefore, an experimenter usually needs to operate at 950° C., and is very likely to be in danger due to any carelessness. The combustion tube is filled with toxic chemicals such as lead chromate, and after the combustion tube bursts, these toxic chemicals are completely exposed to the air and are more likely to contact an experimenter, thus causing a great harm to the human body at a high temperature. At present, neither sea-related universities and research institutions in China nor foreign instrument manufacturers have favorable solutions for this phenomenon. A common analysis method for such samples is to use a domestic combustion tube instead, where a specified number of samples are accumulated and then subjected to centralized measurement with the domestic combustion tube. This method avoids the phenomenon that a combustion tube will crack or burst after being repeatedly used and a bad consequence caused by the phenomenon. This method can reduce a cost by about 60% than the method using the original consumable, but still leads to a cost waste of about 30% than the measurement of a conventional sample. In addition, compared with imported consumables, domestic consumables are more likely to affect analysis results due to impure quartz.

In addition, in the ocean carbon pool, a dissolved organic carbon (DOC) content can often be 4 to 10 times a POC content; and an analysis method of POC and PN specified in a national standard does not consider the influence of DOC adhered to a filter membrane on a sample result. In the analysis of POC and PN contents formerly, various methods were tried to determine the influence of DOC and a sampling method of a blank value, and finally, it was verified through experiments that DOC would pose a great impact on a sample and blank values obtained by different sampling methods would have significant differences. Therefore, the elemental content analysis method of POC and PN is improved on the basis of the national standard, that is, the method of blank value calibration is used in elemental analysis. However, due to the particularity of isotope analysis, a sample will be completely sent to a detection magnetic field after being completely burned by an instrument, the particulate state and the dissolved state cannot be separated, and the influence of DOC cannot be deducted from an obtained isotope ratio by the method of elemental analysis and integral calculation. The detection of stable isotopes obviously cannot use a blank value for correction. Therefore, how to effectively remove DOC adsorbed by a filter membrane during a sampling process is the key to determining the data accuracy.

SUMMARY

In view of the problems existing in current detection of POC and PN in seawater using EA-IRMS, the present disclosure considers the whole process of sample collection, sample storage, sample treatment, and sample detection and changes instrument settings and parameters to reduce a detection cost by 30% and improve the data accuracy and work efficiency.

The present disclosure is implemented in the following way:

A method for analyzing stable isotopes of POC and nitrogen in seawater using EA-IRMS is provided, including the following steps:

a. material preparation: burning a φ25 mm GF/F glass fiber filter membrane at 450° C. for 5 h in advance before use;

b. sample collection: collecting a water sample at a desired station and in a desired layer; using the filter membrane to filter 200 mL of the water sample and then filter 100 ml of distilled water; and wrapping a resulting membrane sample with tin foil, and storing the resulting membrane sample at −20° C. for later use;

c. sample pretreatment: subjecting the membrane sample to acidification for 30 min, drying an acidified membrane sample in a drying oven at 60° C. for 24 h immediately after the acidification, and storing a dried membrane sample in a desiccator;

d. sample coating: coating the membrane sample obtained in step c, and letting a coated membrane sample to be ready for test on a machine;

e. sample determination: cleaning and debugging an elemental analyzer and an isotope ratio mass spectrometer according to operational provisions of the instruments to make the instruments in a sample test status; adjusting general settings of the instruments as follows: setting an oxygen addition time to 80 s and a combustion tube temperature to 700° C. for the elemental analyzer, and modifying ion source parameters and setting a trap current to 300 μA to 400 μA for the isotope ratio mass spectrometer; and starting a sample test;

f. sample loading order: adding three or more isotopic standards certified by the International Atomic Energy Agency (IAEA) or working standards with stable isotope values, where 5 to 6 replicates are set for each standard; adding the sample, where a standard is added every 10 samples; and after all samples are added, starting the instruments for test; and g. sample data processing: observing whether 5 to 6 results of each standard are stable, where if a standard deviation (SD) is lower than 0.2, data are available; if test results of the standards are stable, averaging the 5 to 6 results of each standard; using Excel to plot a standard curve with an average value measured by the instruments as an x-coordinate and a true value as a y-coordinate; and substituting a measured value of a sample into the standard curve for calculation to obtain a true value of the sample, substituting a measured value of a standard inserted among all samples into the standard curve for calculation, and comparing a result with the true value, where if a correction coefficient is in a range of 0.9 to 1.1, it indicates that data are credible.

Compared with the prior art, the present disclosure has the following beneficial effects:

1. In combination with the research on the blank value calibration method during elemental analysis, the present disclosure determines a sampling method that can conveniently and effectively eliminate the influence of DOC on a sample in a sampling stage through experimental comparison. That is, after suction filtration of a sample, suction filtration is conducted for 100 ml of distilled water. This method can realize that an element detection value of a sample is directly equal to a sample value corrected by the blank value calibration method without suction filtration of distilled water, and requires the least distilled water consumption. The present disclosure lowers a work intensity, improves the accuracy of an analysis result, and avoids the influencing factors that are not considered in the national standard of elemental analysis.

2. Through the research on the setting of instrument parameters and the establishment of a standard curve method in the present disclosure, a subversive idea of changing an instrument temperature setting is proposed, and 700° C. is determined as the optimal instrument setting temperature for such samples through experiments. The temperature can not only ensure the complete combustion of a sample, but also realize the reuse of a combustion tube. In an experimental verification process, a breakage rate is almost reduced to 0, which improves a service life of an instrument, and a detection cost for each sample can be reduced by 30%. Data are corrected using a standard curve to control the data quality and ensure the reliability of data after an instrument temperature is changed, which refutes the doubt of a factory engineer that data obtained at a changed temperature are incredible. Moreover, the present disclosure reduces the work intensity and requirements for the inspectors in detection of such samples.

3. In combination with previous device inventions of the applicants related to such instruments, the present disclosure considers the entire process from sample sampling to analysis and establishes a complete set of steps for analyzing stable isotopes of POC and PN in seawater, which improves the work efficiency and data reliability and fills the gap that there is no relevant sample detection method at home and abroad.

DETAILED DESCRIPTION OF THE EMBODIMENTS

Figure 1:
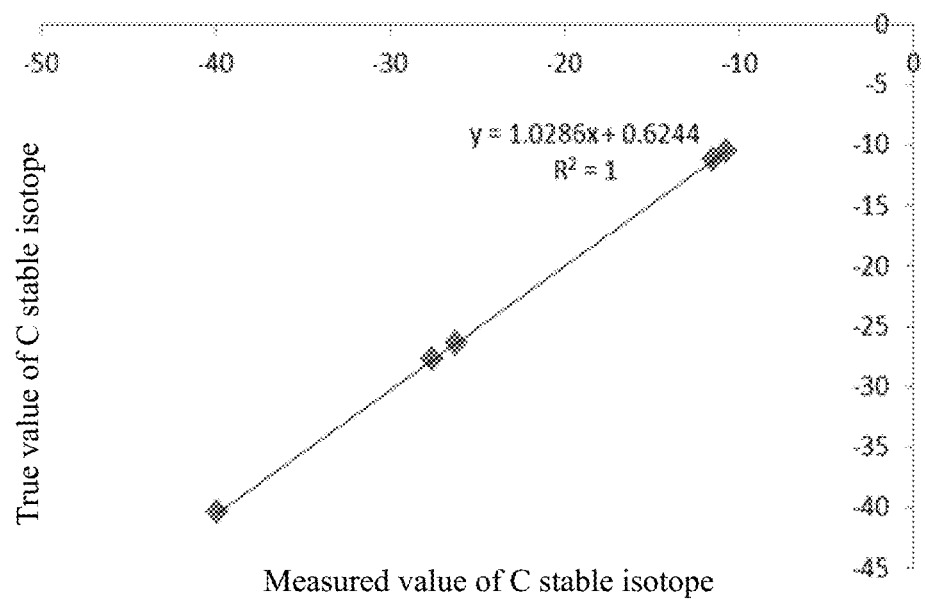
FIG. 1 shows a relationship between a measured value and a true value of a C stable isotope standard.

The technical solutions of the present disclosure will be further described below with reference to examples, but the protection scope of the present disclosure is not limited by the examples in any manner.

Example 1

In this example, a large number of experiments on the influence of temperature on data results and combustion tube burst were conducted, and finally it was determined that a temperature of the technical solution of the present disclosure was set to 700° C. During an experimental process, it was found that, when a temperature was lower than 700° C., incomplete combustion would occur, a resulting standard curve had poor linearity, and after a standard subsequently inserted was substituted into the standard curve, a resulting correction factor was large. Therefore, it was believed that a working temperature of the instrument should not be lower than 700° C. It should be noted that, at 700° C., an oxygen addition time of the instrument should be extended by 10 s to ensure complete combustion. When a temperature was higher than 700° C., it was found by statistics that the occurrence probability of combustion tube crack or burst at 850° C. reached more than 90% as that at 950° C.; and at 750° C. and 800° C., there was also a specified probability to occur burst, where a burst probability reached about 50% at 800° C. and reached about 20% to 30% at 750° C. More than 20 consecutive experiments were conducted at 700° C. in a laboratory, and no burst occurred.

Example 2

In this example, experiments on the influence of oxygen addition time on data results were conducted, and finally it was determined that a temperature of the technical solution of the present disclosure was set to 700° C. In this example, during the test of oxygen addition time of the instrument, when a normal oxygen addition time was set to 70 s, C and N conversion rates of a standard were respectively 99.1% and 99.2% at 700° C.; and after an oxygen addition time was changed to 80 s, C and N conversion rates of a standard were respectively 100.2% and 99.6% at 700° C. Therefore, when the temperature is set to 700° C., an oxygen addition time should be extended by 10 s to ensure complete combustion of a sample.

Example 3

1. Materials and Methods
1.1 Materials
1.1.1 Filter Membrane

On Jun. 2, 2019, a φ25 mm GF/F glass fiber filter membrane was prepared in a laboratory, then burnt in a muffle furnace at 450° C. for 5 h, and taken out and cooled in an electronic moisture-proof box for later use.

1.1.2 Water Sample

On Jun. 4, 2019, surface and bottom seawater samples were collected in an aquaculture area of Dongchu Island Aquatic Products Co., Ltd. in Rongcheng City, Shandong Province, and then transported back to the laboratory and immediately subjected to suction filtration.

1.2 Method
1.2.1 Sample Collection

First, in order to determine a sampling method for stable isotope detection, an element detection experiment was conducted. 4 blank experimental groups and 4 distilled-water suction-filtration experimental groups were set, and corresponding samples were collected to determine the influence of DOC on an elemental analysis result and a reasonable stable isotope sampling method. Specifically: A method of dipping a blank membrane with filtrate drops: after suction filtration was completed, 3 to 5 drops of a resulting filtrate (ensuring that a membrane surface would be wetted) were pipetted with a pipette and added to another blank new membrane, which served as a blank value. A method of completely immersing a blank membrane: after suction filtration was completed, a blank new membrane was completely immersed in a resulting filtrate for 1 s to 2 s and then taken out, which served as a blank value. A double-layer membrane method: Suction filtration was conducted with two stacked membranes, and the second filter membrane layer served as a blank value. A method of conducting suction filtration two times: after suction filtration was completed, a resulting filtrate was completely filtered through a blank new membrane, which served as a blank value. A distilled-water suction-filtration method: after a water sample was subjected to suction filtration with a membrane, and then a specified volume of distilled water was subjected to suction filtration with the original membrane, where the volume of distilled water was set to 50 ml, 100 ml, 150 ml, and 200 ml. 6 replicates were set for each blank experimental group, and 3 replicates were set for each distilled-water suction-filtration group.

A total of 20 stations were set for this survey, and after the sampling method was determined, a sample was prepared according to a corresponding method for test.

1.2.2 Sample Pretreatment

The pretreatment of a sample mainly refers to a process of removing inorganic carbon by acidification. With reference to literatures and national standards, it was found through experimental analysis that an acidification time of 30 min proposed in the national standards and literatures was the optimal, and a too short or too long acidification time would affect the data accuracy. However, acidification is generally achieved by placing a sample and concentrated hydrochloric acid in a closed container, which will cause specified damage to the health of an operator and will also cause a waste of concentrated hydrochloric acid due to volatilization. Therefore, in the early work, a closed multi-layer acid fumigation device with controlled release of acid vapor (ZL201610938287.1) was designed and invented by the inventors. This device can effectively improve the work efficiency and reduce the harm of released acid vapor. Specific operation steps are detailed in the description of this patent. A sample was subjected to acidification for 30 min, then dried in a drying oven at 60° C. for 24 h as soon as possible, and stored in an electronic moisture-proof box.

1.2.3 Sample Coating

An acidified filter membrane needs to be coated before being loaded on a machine for test. A traditional coating tool is inefficient. In the early work, a sample coating device for an elemental analyzer (ZL201410534476.3) was also designed and invented by the inventors. This device can improve the work efficiency, increase a success rate of sample coating, and achieve other functions. Operation steps are detailed in the description of this patent. A coated sample is ready for test on the machine.

1.2.4 Sample Determination

Before instruments were started, an ash tube was first cleaned and the activity of a reduction tube was checked for the elemental analyzer (EL cube, German elementar); after requirements were met, the system was started and subjected to leakage detection; after the leakage detection was passed, a blank value of the instrument was tested; the isotope ratio mass spectrometer (vario Micro cube-ISOprime 100) was started; and after the system was subjected to vacuum-pumping, linearity and stability tests were conducted for the mass spectrometer to make it in a sample test state. Then the general settings of the instruments were modified as follows:

for the elemental analyzer, an oxygen addition time was changed from 70 s to 80 s and a combustion tube temperature was changed from 950° C. to 700° C.; and for the isotope ratio mass spectrometer, ion source parameters were modified, a trap current was changed from 200 μA to 300-400 μA, and other parameters were unchanged. The sample test was started. Three or more isotopic standards certified by the International Atomic Energy Agency (IAEA) or working standards with stable isotope values were first added, where the isotopic standards certified by the International Atomic Energy Agency (IAEA) were IAEA-N-2, IAEA-600, and IAEA-CH-6, the working standards were L-phenylalanine, USGS40, and EDTA #2, and 5 to 6 replicates were set for each standard; then a sample to be tested was added, where a standard was added every 10 samples; and after all samples were added, the instruments were started for test.

2. Results and Discussion 2.1 Sample Collection

According to different experimental groups, a sample value and a blank value were obtained through elemental analysis to determine a sample collection method for stable isotope analysis. Experimental results were shown in Table 1. According to analysis of the experimental results, blank values obtained by the method of completely immersing a blank membrane and the double-layer membrane method are the highest, where a blank value may be higher than a sample value. In actual operation, repeated sampling is difficult to achieve at each survey station, and thus the probability that data are unavailable due to a blank value being higher than a sample value is greatly increased. Therefore, the above two blank value sampling methods are inadvisable. Among the remaining methods, the method of dipping a blank membrane with filtrate drops has the optimal effect, where blank values of 6 replicates are the most stable; results of the method of conducting suction filtration two times are similar to results of the method of dipping a blank membrane with filtrate drops, but there are abnormal values in the 6 replicates; and results of the distilled-water suction-filtration method at 4 different distilled water volumes show that, after suction filtration is conducted for 50 ml of distilled water, a calculated value is slightly higher than an average value of the method of dipping a blank membrane with filtrate drops, and results of the experimental groups using 100 ml, 150 ml, and 200 ml of distilled water show no significant difference, and are similar to data corrected with the blank values of the method of dipping a blank membrane with filtrate drops and the method of conducting suction filtration two times. According to the above-mentioned experimental analysis, the method of dipping a blank membrane with filtrate drops, the 100 ml distilled-water method, and the method of conducting suction filtration two times lead to the optimal effect. Given that the isotope analysis cannot use the blank value correction method, in a sample collection process for detecting stable isotopes of POC and PN in seawater, after a sample is subjected to suction filtration with a membrane, 100 ml of distilled water must be subjected to suction filtration with the same membrane.

TABLE 1

Results of the blank value sampling methods

| | Measured value (mg) | | Blank value (mg) | | Calculated value (mg/L) | |
| --- | --- | --- | --- | --- | --- | --- |
| Sample No. | C | N | C | N | POC | PN |
| Method of dipping a blank membrane with filtrate drops-1 | 12.81 | 7.50 | 5.54 | 2.70 | 0.3635 | 0.24 |
| Method of dipping a blank membrane with filtrate drops-2 | 12.39 | 7.42 | 5.86 | 2.68 | 0.3265 | 0.237 |
| Method of dipping a blank membrane with filtrate drops-3 | 12.35 | 7.75 | 5.36 | 2.02 | 0.3495 | 0.2865 |
| Method of dipping a blank membrane with filtrate drops-4 | 12.50 | 7.72 | 5.45 | 2.21 | 0.3525 | 0.2755 |
| Method of dipping a blank membrane with filtrate drops-5 | 12.58 | 7.11 | 5.15 | 2.22 | 0.3715 | 0.2445 |
| Method of dipping a blank membrane with filtrate drops-6 | 12.39 | 7.53 | 5.61 | 2.66 | 0.339 | 0.2435 |
| Average value | 12.50 ± 0.17 | 7.51 ± 0.23 | 5.50 ± 0.24 | 2.42 ± 0.30 | 0.35 ± 0.02 | 0.25 ± 0.02 |
| Method of completely immersing a blank membrane-1 | 12.14 | 7.89 | 6.93 | 16.83 | 0.2605 | / |
| Method of completely immersing a blank membrane-2 | 12.28 | 6.22 | 6.26 | 3.96 | 0.301 | 0.113 |
| Method of completely immersing a blank membrane-3 | 12.31 | 7.51 | 15.85 | 7.48 | / | 0.0015 |
| Method of completely immersing a blank membrane-4 | 12.99 | 6.81 | 6.19 | 3.80 | 0.34 | 0.1505 |
| Method of completely immersing a blank membrane-5 | 12.22 | 7.30 | 9.42 | 5.25 | 0.14 | 0.1025 |
| Method of completely immersing a blank membrane-5 | 13.05 | 7.19 | 6.48 | 6.75 | 0.3285 | 0.022 |
| Average value | 12.49 ± 0.41 | 7.15 ± 0.58 | 8.52 ± 3.79 | 7.35 ± 4.87 | 0.27 ± 0.20 | 0.08 ± 0.22 |
| Double-layer membrane method-1 | 13.27 | 6.39 | 14.71 | 3.18 | / | 0.1605 |
| Double-layer membrane method-2 | 13.33 | 6.67 | 7.86 | 3.04 | 0.2735 | 0.1815 |
| Double-layer membrane method-3 | 14.06 | 5.08 | 7.29 | 3.50 | 0.3385 | 0.079 |
| Double-layer membrane method-4 | 13.44 | 6.03 | 9.49 | 4.01 | 0.1975 | 0.101 |
| Double-layer membrane method-5 | 13.24 | 6.65 | 3.46 | 7.46 | 0.489 | / |
| Double-layer membrane method-6 | 12.44 | 3.83 | 12.88 | 3.88 | / | / |

TABLE 1-continued

Results of the blank value sampling methods

| Sample No. | Measured value (mg) C | N | Blank value (mg) C | N | Calculated value (mg/L) POC | PN |
|---|---|---|---|---|---|---|
| Average value | 13.30 ± 0.52 | 5.78 ± 1.12 | 9.28 ± 4.06 | 4.18 ± 1.65 | 0.32 ± 0.22 | 0.13 ± 0.09 |
| Method of conducting suction filtration two times-1 | 12.18 | 7.11 | 5.67 | 2.92 | 0.3255 | 0.2095 |
| Method of conducting suction filtration two times-2 | 12.72 | 7.31 | 5.84 | 3.05 | 0.344 | 0.213 |
| Method of conducting suction filtration two times-3 | 12.13 | 7.82 | 8.05 | 3.05 | 0.204 | 0.2385 |
| Method of conducting suction filtration two times-4 | 12.75 | 7.22 | 10.34 | 2.47 | 0.1205 | 0.2375 |
| Method of conducting suction filtration two times-5 | 12.49 | 7.66 | 5.17 | 3.12 | 0.366 | 0.227 |
| Method of conducting suction filtration two times-6 | 12.92 | 7.22 | 5.01 | 2.81 | 0.3955 | 0.2205 |
| Average value | 12.53 ± 0.32 | 7.39 ± 0.28 | 6.68 ± 2.10 | 2.90 ± 0.23 | 0.29 ± 0.11 | 0.22 ± 0.01 |
| 50 ml distilled water-1 | 7.99 | 5.73 | / | / | 0.3995 | 0.2865 |
| 50 ml distilled water-2 | 7.53 | 5.51 | / | / | 0.3765 | 0.2755 |
| 50 ml distilled water-3 | 8.00 | 5.80 | / | / | 0.4 | 0.29 |
| Average value | 7.84 ± 0.27 | 5.68 ± 0.15 | / | / | 0.39 ± 0.01 | 0.28 ± 0.01 |
| 100 ml distilled water-1 | 7.09 | 4.73 | / | / | 0.3545 | 0.2365 |
| 100 ml distilled water-2 | 6.93 | 5.01 | / | / | 0.3465 | 0.2505 |
| 100 ml distilled water-3 | 7.00 | 5.30 | / | / | 0.35 | 0.265 |
| Average value | 7.01 ± 0.08 | 5.01 ± 0.29 | / | / | 0.35 ± 0.01 | 0.25 ± 0.01 |
| 150 ml distilled water-1 | 7.07 | 5.03 | / | / | 0.3535 | 0.2515 |
| 150 ml distilled water-2 | 7.10 | 5.05 | / | / | 0.355 | 0.2525 |
| 150 ml distilled water-3 | 7.01 | 5.12 | / | / | 0.3505 | 0.256 |
| Average value | 7.06 ± 0.05 | 5.07 ± 0.05 | / | / | 0.35 ± 0.01 | 0.25 ± 0.01 |
| 200 ml distilled water-1 | 7.02 | 4.77 | / | / | 0.351 | 0.2385 |
| 200 ml distilled water-2 | 6.91 | 4.91 | / | / | 0.3455 | 0.2455 |
| 200 ml distilled water-3 | 6.92 | 5.02 | / | / | 0.346 | 0.251 |
| Average value | 6.95 ± 0.06 | 4.90 ± 0.13 | / | / | 0.34 ± 0.01 | 0.24 ± 0.01 |

2.2 Sample Determination

Figure 2:
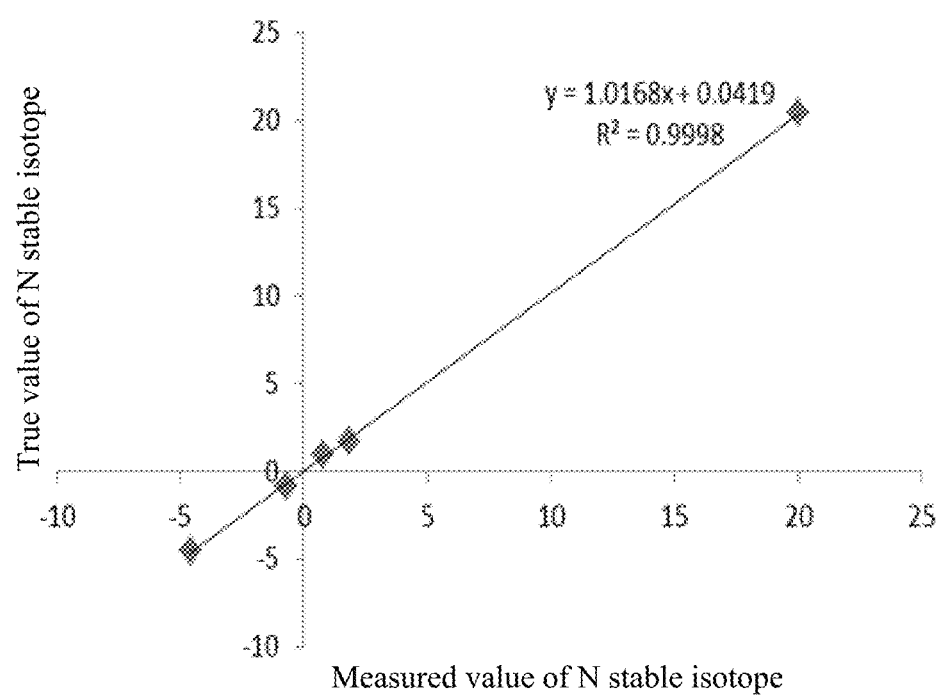
FIG. 2 shows a relationship between a measured value and a true value of an N stable isotope standard.

After the stable isotope detection was completed, standard curves illustrating a relationship between a measured value and a true value of an isotope ratio of a standard were plotted and shown in FIG. 1 and FIG. 2. It can be seen from the standard curves that a measured value of an instrument had a prominent linear correlation with a true value. In this experiment, a total of 20 seawater samples were collected, and 2 standards were inserted (the standard IAEA-600 certified by the International Atomic Energy Agency (IAEA) was adopted: $\delta^{15}N=1$ and $\delta^{13}C=-27.771$). A measured value of a seawater sample was substituted into the C and N standard curves separately to obtain true values of the sample. Moreover, in order to verify the credibility of test data, a measured value of a standard was substituted into the standard curves to obtain stable isotopes of carbon and nitrogen: C (−27.66, −27.74) and N (0.99, 1), and correction factors were both close to 1. Therefore, the method and operation of the present disclosure are accurate, convenient, and highly feasible.

What is claimed is:

1. A method for analyzing stable isotopes of particulate organic carbon (POC) and nitrogen in seawater using elemental analysis-isotope ratio mass spectrometry (EA-IRMS), comprising the following steps:

a. material preparation: burning a φ25 mm GF/F glass fiber filter membrane at 450° C. for 5 h in advance before use;

b. sample collection: collecting a water sample at a desired station and in a desired layer; using the φ25 mm GF/F glass fiber filter membrane to filter 200 mL of the water sample and then filter 100 ml of distilled water; and wrapping a resulting membrane sample with tin foil, and storing the resulting membrane sample at −20° C. for later use;

c. sample pretreatment: subjecting the resulting membrane sample to acidification for 30 min to obtain an acidified membrane sample, drying the acidified membrane sample in a drying oven at 60° C. for 24 h immediately after the acidification to obtain a dried membrane sample, and storing the dried membrane sample in a desiccator;

d. sample coating: coating the dried membrane sample obtained in step c to obtain a coated membrane sample, and letting the coated membrane sample to be ready for test on a machine;

e. sample determination: cleaning and debugging instruments of an elemental analyzer and an isotope ratio mass spectrometer according to operational provisions of the instruments to make the instruments in a sample test status; adjusting general settings of the instruments as follows: setting an oxygen addition time to 80 s and a combustion tube temperature to 700° C. for the elemental analyzer, and modifying ion parameters and setting a trap current to 300 µA to 400 µA for the isotope ratio mass spectrometer; and starting a sample test;

f. sample loading order: adding three or more isotopic standards certified by the International Atomic Energy Agency (IAEA) or working standards with stable isotope values, wherein 5 to 6 replicates are set for each standard of the isotopic standards and the working standards; adding the coated membrane sample, wherein a standard is added every 10 samples; and after all samples are added, starting the instruments for test; and g. sample data processing: observing whether 5 to 6 results of the each standard are stable, wherein if a standard deviation (SD) is lower than 0.2, data are available; if test results of the isotopic standards and the working standards are stable, averaging the 5 to 6 results of the each standard; using Excel to plot a standard curve with an average value measured by the instruments as an x-coordinate and a true value as a y-coordinate; and substituting a measured value of a sample into the standard curve for calculation to obtain a true value of the sample, substituting a measured value of a standard inserted among all samples into the standard curve for calculation, and comparing a result with the true value, wherein if a correction coefficient is in a range of 0.9 to 1.1, data are credible.

* * * * *